United States Patent
Ma et al.

(10) Patent No.: US 11,761,001 B2
(45) Date of Patent: Sep. 19, 2023

(54) MBP_ARGONAUTE PROTEINS FROM PROKARYOTES AND APPLICATIONS THEREOF

(71) Applicant: Hubei University, Wuhan (CN)

(72) Inventors: Lixin Ma, Wuhan (CN); Wenqiang Li, Wuhan (CN); Fei Wang, Wuhan (CN); Ruyi He, Wuhan (CN); Yang Liu, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 17/854,897

(22) Filed: Jun. 30, 2022

(65) Prior Publication Data
US 2022/0389425 A1    Dec. 8, 2022

Related U.S. Application Data

(63) Continuation of application No. PCT/CN2022/070424, filed on Jan. 6, 2022.

(30) Foreign Application Priority Data

May 25, 2021 (CN) .......................... 202110581929.8

(51) Int. Cl.
*C12N 9/22* (2006.01)
*C12N 15/113* (2010.01)

(52) U.S. Cl.
CPC .............. *C12N 15/113* (2013.01); *C12N 9/22* (2013.01)

(58) Field of Classification Search
CPC ..................................................... C12N 9/22
See application file for complete search history.

(56) References Cited

PUBLICATIONS

Sheng et al. Structure-based cleavage mechanism of Thermus thermophilus argonaute DNA guide strand-mediated DNA target cleavage. Proceedings of the National Academy of Sciences, USA, vol. 111, No. 2, pp. 652-657, and pp. 1-19 of Supplemental Information, Jan. 14, 2014. (Year: 2014).*
Pankratov et al. International Journal of Systematic and Evolutionary Microbiology, vol. 57, pp. 2349-2354, 2007. (Year: 2007).*
What are the concentrations of different ions in cells? Printed from http://book.bionumbers.org/what-are-the-concentrations-of-different-ions-in-cells, as pp. 1/5-5/5 on Dec. 20, 2016. (Year: 2016).*
GenPept, Login No. WP_008504757.1, Jun. 5, 2013, printed as pp. 1/3-3/3.
Sergei Ryazansky, etc., "The Expanded Universe of Prokaryotic Argonaute Proteins", Molecular Biology and Physiology, vol. 19, issue 6, pp. e-01935-18, printed as pp. 1-20, Dec. 2018.

* cited by examiner

*Primary Examiner* — Jennifer Dunston
(74) *Attorney, Agent, or Firm* — WPAT, PC

(57) ABSTRACT

Mbp_Argonaute proteins from prokaryotes and application thereof are provided. The Mbp_Argonaute protein consists of an amino acid sequence as shown in SEQ ID NO: 1 or a sequence with at least 50% or at least 80% of homology with the amino acid sequence as shown in SEQ ID NO: 1. An Argonaute protein gene derived from a cold-resistant prokaryote *Mucilaginibacter paaluis* is synthesized and named as MbpAgo, which has binding activity to single-stranded guide DNA and has nuclease activity to target RNA and/or target DNA complementarily paired with the single-stranded guide DNA, the MbpAgo can be used for the target RNA editing in vivo and in vitro to achieve site-specific modification of genetic material. The MbpAgo can modify highly-structured RNAs and not affect an endogenous RNAi pathway of animal and plant cells, provides a new and powerful tool for RNA editing with high cleavage activity and good specificity.

9 Claims, 4 Drawing Sheets

Specification includes a Sequence Listing.

| Protein | Source | | | | | | Identity(%) |
|---|---|---|---|---|---|---|---|
| hAgo2 | -Homo sapiens | SEQ ID NO: 3 | FLCAVTHP | QHRQE-IIQD | IPYPDDVBB | AYYARLVAF | 15.04 |
| KpAgo | -Kluyveromyces Polysporus | SEQ ID NO: 4 | VLGSDVTHY | DSNSBITTN | MYERGVSV | VYYALLCT | 15.55 |
| RsAgo | -Rhodobacter Sphaeroides | SEQ ID NO: 5 | WQMELAEL | EYEGT---SD | VFHARPLK | IFYSPPIAE | 13.14 |
| PfAgo | -Pyrococcus furiosus | SEQ ID NO: 6 | IIGIVAPM | EQRGESVRMN | LLLREGRIT | VHYAKFAN | 16.51 |
| MjAgo | -Methanocaldococcus jannaschii | SEQ ID NO: 7 | IMSLIPSLS | AP-GERIKLS | LFIRLGFIQ | IHYALKFVK | 16.27 |
| TtAgo | -Thermus thermophilus | SEQ ID NO: 8 | AVGFRAGGR | -QAGFRIPQE | LLLREGPVP | LHLALKFVK | 17.62 |
| SeAgo | -Synechococcus elongates | SEQ ID NO: 9 | IIGFVTGTN | -QRGTFSGQ | LIMRLGLVQ | LHLARSSK | 15.35 |
| MpAgo | -Marinitoga piezophila | SEQ ID NO: 10 | YIGIELSHD | -ELNRKMNLD | FILRLGRPI | LRIAIKVAL | 14.97 |
| NgAgo | -Natronobacterium gregoryi | SEQ ID NO: 11 | FIGIVSHS | -QLGKLQST | VFHPIGRMN | TAYAQQASF | 16.72 |
| LrAgo | -Limnothrix rosea | SEQ ID NO: 12 | IVGLDVSPR | -IDSILFEH | LHRLGLFP | TYYAKIST | 16.44 |
| CbAgo | -Clostridium butyricum | SEQ ID NO: 13 | FIGLVGTR | -QSGFKIAET | VIHRLGFSR | TGYAIKICK | 18.83 |
| CbcAgo | -Clostridium. butyricum CWBI1009 | SEQ ID NO. 14 | FIGLVGTR | -QSGFKIAET | VIHRLGFSR | TGYAIKICK | 18.83 |
| CpAgo | -Clostridium perfringens | SEQ ID NO: 15 | FVGLVGTR | -QNSEKINFE | VIRRLGFSR | TGYAIKICK | 17.53 |
| IbAgo | -Intestinibacter bartlettii | SEQ ID NO: 16 | YIGLIVC-R | -QSGFKIQIN | VFHPLGINR | TYYALSSI | 16.89 |
| KmAgo | -Kurthia massiliensis | SEQ ID NO. 17 | FIGIVS-B | -LASRKIDDY | THRLGFWK | IHYALLSAT | 17.41 |
| MbpAgo | -Mucilaginibacter paludis | SEQ ID NO: 18 | YIGIAVHDR | SQRVEKVRAK | VIVRLGPSF | IKLIPTLLE | 100 |
| MbpAgo_DM | -Mucilaginibacter paludis double mutant | SEQ ID NO: 19 | YIGLAVHDR | SQEVEKVPAK | VIVRLGRSF | IKLIPTLLE | |

FIG. 3

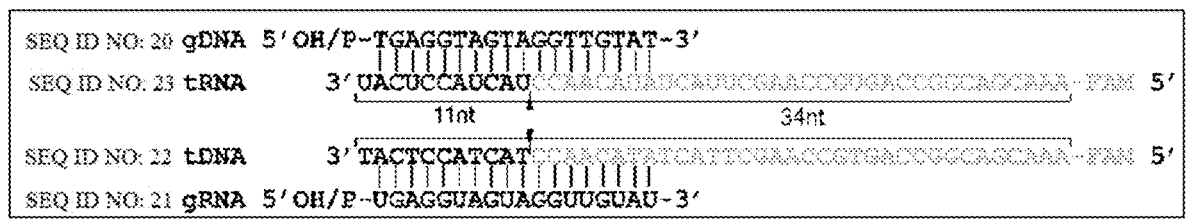

FIG. 4

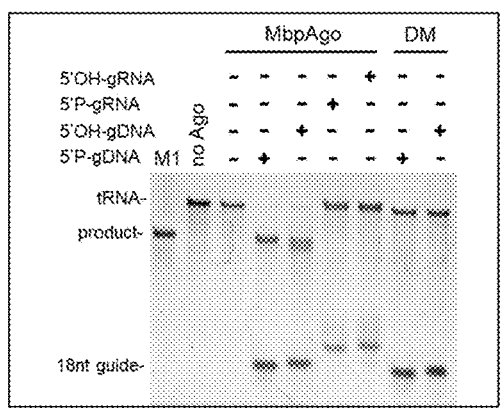

FIG. 5

SEQUENCE LISTING

```
<160> NUMBER OF SEQ ID NOS: 23

<210> SEQ ID NO 1
<211> LENGTH: 795
<212> TYPE: PRT
<213> ORGANISM: Artificial sequence
<220> FEATURE:
<223> OTHER INFORMATION: Mucilaginibacter paludis

<400> SEQUENCE: 1

Met Lys Asp His Ile Leu Asn Leu Tyr Arg Ile Asp Asn Leu Ser Glu
1               5                   10                  15

Leu Asp Phe Ser Tyr Lys Leu Ile Asp Phe Asp Leu Ser Phe Ile Ala
            20                  25                  30

Gly Lys Glu Glu Leu Leu Asn Lys Gln Leu Gln Lys Ile Ala Glu Glu
        35                  40                  45

Val Ser Ser Val Thr Lys Gly Pro Thr Ala Val Leu Lys Arg Asn Gln
    50                  55                  60

Arg Phe Phe Val Ala Val Pro Ala Asp Lys Gln Met Glu Asp Arg Ser
65                  70                  75                  80

Ile Asp Gly Ile Pro Phe Ser Ile Pro Lys Leu Leu Pro Glu Val
                85                  90                  95

Tyr Arg Ile Asp Ser Lys Asp Ile Gln Gly His Gln Leu Asp Val Val
                100                 105                 110

Tyr Lys Phe Leu Asp Tyr Glu Ile Arg Arg Gln Leu Gly Gln His Arg
            115                 120                 125

Asp Leu Trp Lys Leu Asn Thr His Gln Phe Phe Leu Arg Glu Pro Met
        130                 135                 140

Lys Gly Ile Gln Gly Ser Ile Asn Val Phe Glu Gly Phe Thr Tyr Lys
145                 150                 155                 160

Leu Ala Arg Leu Ala Asp Gly His Phe Tyr Val Thr Leu Asp Leu Ser
                165                 170                 175

Thr Lys Tyr Ile Asp Lys Tyr Cys Leu Ser His Tyr Ile Asn Glu Gly
                180                 185                 190

Asn Val Arg Thr Phe Glu Asn Asn Tyr Lys Gly Arg Arg Phe Leu Tyr
            195                 200                 205

Leu Asn Gly Asp Asn Trp Tyr Thr Ile Glu Leu Leu Gly Phe Gly Lys
        210                 215                 220

Ser Val Lys Glu Gln Asp Phe Ile Arg Glu Gly Thr Thr Tyr Asn Val
225                 230                 235                 240

Leu Asn Tyr Ile Thr Glu Lys Ile Glu His Ser Arg Thr Asp Leu Lys
                245                 250                 255

Arg Tyr Val Lys Pro Asn Asp Leu Ser Met Ser Tyr Thr Tyr Pro Gly
                260                 265                 270

Arg Thr Met Asp Pro His Ser Gly Ala Thr Ser Leu Ala Arg Met Leu
            275                 280                 285

Tyr Asn Thr Lys Asp Glu Arg Val Lys Ser Leu His Tyr Leu Ser Ile
        290                 295                 300

Lys Gly Pro Ser Lys Arg Phe Glu Ala Ile Asn Asn Tyr Ile Ser Ser
305                 310                 315                 320
```

```
Tyr Phe Lys Asn Leu Lys Phe Asn Ala Gly Lys Leu Leu Ile Ser Asn
                325                 330                 335
Glu Pro Leu Val Glu Lys Ile Lys Asn Phe Trp Ile Pro Glu Leu Leu
                340                 345                 350
Phe Asn Asn Asn Arg Arg Leu Lys Ile Thr Gly Phe Asn Ser Gly Met
                355                 360                 365
Arg Asp Phe Ala Tyr Gln Arg Lys Gln Leu Ile Lys Asn Asn Gly Val
            370                 375                 380
Leu Asn Arg Thr Ser Phe Asp Val Gln Tyr Leu Leu Val Pro Asp Glu
385                 390                 395                 400
Gln Tyr Met Asp Ala Asn Leu Val Glu Gly Phe Lys Asn Asn Ala Glu
                405                 410                 415
Phe Leu Ile Lys Lys Leu Ala Pro Ala Phe Asp Lys Phe Ile Ile Ile
                420                 425                 430
Arg Tyr Pro Val Lys Ser Cys Thr Ser Ala Ser Val Gln Ile Gln Glu
            435                 440                 445
Ile Glu Lys Val Leu His Arg Arg Asn Ala Leu His Gly Phe Ala Leu
        450                 455                 460
Val Val Leu Pro Asp Leu Asp Ala Phe Ser Pro Ala Phe Leu Lys Thr
465                 470                 475                 480
Phe His Glu Leu Leu Lys Ser Lys Phe Tyr Pro Asp Leu Lys Val Gln
                485                 490                 495
Cys Ala Ser Ala His Asn Ile Ser Ser Phe Phe Lys Pro Phe Ser Thr
                500                 505                 510
Ala Gly Asn Asn Gly Ile Val Glu Tyr Arg Val Glu Ala Leu Lys
            515                 520                 525
Gly Arg Phe Ser Ser Tyr Leu Phe Tyr Leu Val Leu Glu His Leu Ile
        530                 535                 540
Val Asn Arg Lys Trp Pro Tyr Ala Leu Ala Lys Asn Leu Phe Tyr Asp
545                 550                 555                 560
Ile Tyr Ile Gly Ile Asp Val His Asp Arg His Ala Gly Phe Thr Phe
                565                 570                 575
Phe Phe Lys Asn Gly Glu Gln Ile Ile Phe His Pro Glu Glu Val Pro
                580                 585                 590
Gln Lys Thr Asn Ser Gln Arg Val Glu Lys Val Arg Ala Lys Thr Leu
            595                 600                 605
Asn Lys Val Ile Tyr Glu Lys Leu Lys Leu Tyr Ile Pro Leu Phe Ala
        610                 615                 620
Pro Asn Pro Asn Gly Ile Val Ile Val Arg Asp Gly Arg Ser Phe Gly
625                 630                 635                 640
Val Glu Tyr Lys Ala Leu Gln Ala Ala Ile Asn Thr Leu Ala Ala Glu
                645                 650                 655
Gly Ile Val Asn Lys Asp Thr Val Lys Tyr Gly Val Val Asp Leu His
                660                 665                 670
Lys Gln Ser Ser Val Pro Ile Arg Ile Ala Ala Lys Thr Asn Ser Tyr
            675                 680                 685
Asp Gln Leu Glu Asn Pro Val Ala Gly Ser Tyr Lys Leu Val Ser Pro
        690                 695                 700
Lys Glu Gly Phe Ile Phe Ser Thr Gly Tyr Pro Phe Asp Ile Lys Gly
705                 710                 715                 720
Thr Ser Arg Pro Leu Asn Leu Ser Met Lys Glu Gly Asp Leu Asp Phe
                725                 730                 735
```

```
Met Lys Val Met Glu Asp Val Phe Cys Gln Ile Met Leu Ala Phe Ser
        740                 745                 750
Ala Pro Asp Lys Ser Asn Phe Leu Pro Val Ile Ile Lys Leu Ile Asp
        755                 760                 765
Thr Leu Leu Glu Pro Leu Thr Ala Thr Arg Glu Thr Ala Asp Glu Ala
        770                 775                 780
Glu Glu Asp Glu Glu Glu Met Met Asp Ile Asn
785                 790                 795

<210> SEQ ID NO 2
<211> LENGTH: 2388
<212> TYPE: DNA
<213> ORGANISM: Artificial sequence
<220> FEATURE:
<223> OTHER INFORMATION: Mucilaginibacter paludis

<400> SEQUENCE: 2
atgaaggacc acatcctgaa cctgtaccgg atcgacaacc tgagcgagct         50
ggacttcagc tacaagctga tcgacttcga cctgagcttt atcgccggca        100
aagaggaact gctgaacaag cagctgcaga aaatcgccga gaggtgtcc         150 agcgtgacaa agggacctac cgccgtgctg aagcggaacc agagattctt        200
tgtggccgtg cctgccgaca gcagatgga agatcggtct atcgacggca         250 tcccttcag catccccatc aagctgctgc cgaggtgta cagaatcgac          300 agcaaggaca tccagggcca ccagctggac gtggtgtaca gttcctgga         350 ctacgagatc agacggcagc tgggccagca cagagatctg tggaagctga        400
acacccacca gttctttctg cgcgagccca tgaagggaat ccagggcagc        450
atcaacgtgt cgagggcttt cacatacaag ctggccagac tggccgacgg        500 ccactttac gtgacactgg acctgagcac caagtacatc gacaagtact         550
gcctgagcca ctcatcaac gagggcaacg tgcggacctt cgagaacaac         600
tacaagggca gaagattcct gtacctgaac ggcgacaact ggtacaccat        650
cgagctgctc ggcttcggca agagcgtgaa agagcaggac ttcatcagag        700
agggcaccac ctacaacgtg ctgaattaca tcaccgagaa gatcgagcac        750
agccggaccg acctgaagag atacgtgaag cccaacgacc tgtccatgag        800
ctacacatac cccggcagaa caatggaccc tcacagcgga gctacatccc        850
tggccagaat gctgtacaac accaaggacg agagagtgaa gtccctgcac        900
tacctgtcta tcaagggccc cagcaagaga ttcgaggcca tcaacaatta        950
catctccagc tacttcaaga acctgaagtt caacgccggg aagctgctga       1000
tctccaacga gcccctggtg aaaagatca agaacttctg gattcctgag        1050
ctgctgttca caacaaccg gcggctgaag atcaccggct tcaacagcgg        1100
catgcgggac ttcgcctacc agagaaagca gctgattaag aacaacgggg       1150
tgctgaacag gaccagcttc gacgtgcagt acctgctggt gcccgacgag       1200
cagtacatgg acgccaatct ggtggaaggg ttcaagaaca tgccgagtt        1250 cctgatcaag aagctggccc ctgccttcga caagttcatc atcatcagat       1300
accccgtcaa gagctgcacc agcgccagcg tgcagatcca agagatcgag       1350
aaggtgctgc acagacggaa tgccctgcac ggatttgctc tggtggtgct       1400
gcctgacctg gacgctttta gccccgcctt cctgaaaacc ttccacgagc       1450
```

```
tgctgaagtc taagttctac cccgatctga aggtgcagtg cgccagcgct      1500
cacaacatct ctagctttt caagcccttc tccaccgccg gcaacaacgg       1550
catcgtcgag tacagagtgg tggaagccct gaagggcaga ttcagctcct      1600
acctgttcta cctggtgctg gaacacctga tcgtgaaccg gaagtggcct      1650
tacgctctgg ccaagaatct gttctacgac atctacatcg gcatcgatgt      1700
gcacgaccgg cacgccggct ttacattctt cttcaaaaac ggcgaacaga      1750
tcatctttca ccccgaggaa gtgccccaga aacaaacag ccagcgcgtg       1800 gaaaagtgc gggccaagac actgaacaaa gtgatctacg agaagctgaa       1850
gctgtacatc ccactgttcg ccctaatcc taatggcatc gtgatcgtcc       1900
gcgacggcag aagctttggc gtcgagtata aggccctgca ggccgccatc      1950
aatactctgg ccgctgaggg aatcgtgaac aaggacaccg tgaagtacgg      2000
cgtggtggac ctgcacaagc agagcagcgt gccaatcaga atcgccgcca      2050
agaccaacag ctacgatcag ctggaaaacc ccgtggccgg ctcctataag      2100
ctggtgtctc ctaaagaggg ctttatcttc agcacaggct accccttcga      2150
catcaagggc acctccagac ctctgaacct gagcatgaag gaaggcgacc      2200
tggactttat gaaagtcatg gaagatgtgt tctgccagat catgctggcc      2250
ttcagcgccc ctgacaagag caacttcctg cctgtgatca tcaaactgat      2300
cgacaccctg ctggaacctc tgaccgccac aagagaaaca gccgacgagg      2350
ctgaagagga cgaagaggaa atgatggaca tcaactag                  2388
```

<210> SEQ ID NO 3
<211> LENGTH: 36
<212> TYPE: PRT
<213> ORGANISM: Artificial sequence
<220> FEATURE:
<223> OTHER INFORMATION: Home sapiens

<400> SEQUENCE: 3

```
Phe Leu Gly Ala Asp Val Thr His Pro Gln His Arg Gln Glu Ile Ile
 1               5                  10                  15

Gln Asp Ile Phe Tyr Arg Asp Gly Val Ser Glu Ala Tyr Tyr Ala His
            20                  25                  30

Leu Val Ala Phe
        35
```

<210> SEQ ID NO 4
<211> LENGTH: 37
<212> TYPE: PRT
<213> ORGANISM: Artificial sequence
<220> FEATURE:
<223> OTHER INFORMATION: Kluyveromyces Polysporus

<400> SEQUENCE: 4

```
Val Leu Gly Ser Asp Val Thr His Tyr Asp Gly Pro Gly Glu Glu Ile
 1               5                  10                  15

Ile Thr Asn Met Tyr Phe Arg Asp Gly Val Ser Val Val Tyr Tyr Ala
            20                  25                  30

Asp Leu Leu Cys Thr
        35
```

<210> SEQ ID NO 5

```
<211> LENGTH: 34
<212> TYPE: PRT
<213> ORGANISM: Artificial sequence
<220> FEATURE:
<223> OTHER INFORMATION: Rhodobacter Sphaeroides

<400> SEQUENCE: 5

Val Val Gly Met Gly Leu Ala Glu Leu Glu Tyr Glu Gly Tyr Ser Asp
1               5                   10                  15

Val Phe His Ala His Arg Pro Leu Lys Ile Phe Tyr Ser Glu Arg Ile
            20                  25                  30

Ala Glu

<210> SEQ ID NO 6
<211> LENGTH: 37
<212> TYPE: PRT
<213> ORGANISM: Artificial sequence
<220> FEATURE:
<223> OTHER INFORMATION: Pyrococcus furiosus

<400> SEQUENCE: 6

Ile Ile Gly Ile Asp Val Ala Pro Met Glu Gln Arg Gly Glu Ser Val
1               5                   10                  15

Asp Met Asn Leu Leu Arg Asp Gly Arg Ile Thr Val His Tyr Ala
            20                  25                  30

His Lys Phe Ala Asn
        35

<210> SEQ ID NO 7
<211> LENGTH: 35
<212> TYPE: PRT
<213> ORGANISM: Artificial sequence
<220> FEATURE:
<223> OTHER INFORMATION: Methanocaldococcus jannaschii

<400> SEQUENCE: 7

Ile Met Gly Leu Asp Thr Gly Leu Gly Ala Pro Gly Glu Arg Leu His
1               5                   10                  15

Leu Pro Leu Phe Leu Arg Asp Gly Phe Ile Gln Ile His Tyr Ala Lys
            20                  25                  30

Phe Val Lys
        35

<210> SEQ ID NO 8
<211> LENGTH: 36
<212> TYPE: PRT
<213> ORGANISM: Artificial sequence
<220> FEATURE:
<223> OTHER INFORMATION: Thermus thermophilus

<400> SEQUENCE: 8

Ala Val Gly Phe Asp Ala Gly Gly Arg Gln Ala Gly Glu Arg Ile Pro
1               5                   10                  15

Gln Glu Leu Leu Leu Arg Asp Gly Arg Val Pro Leu His Leu Ala Asp
            20                  25                  30

Arg Leu Val Lys
        35

<210> SEQ ID NO 9
<211> LENGTH: 36
<212> TYPE: PRT
<213> ORGANISM: Artificial sequence
<220> FEATURE:
```

<223> OTHER INFORMATION: Synechococcus elongates

<400> SEQUENCE: 9

Ile Ile Gly Phe Asp Thr Gly Thr Asn Gln Arg Gly Glu Thr Phe Ser
1               5                   10                  15

Gly Gln Leu Leu Met Arg Asp Gly Leu Val Gln Leu His Leu Ala Asp
            20                  25                  30

Arg Ser Ser Lys
        35

<210> SEQ ID NO 10
<211> LENGTH: 36
<212> TYPE: PRT
<213> ORGANISM: Artificial sequence
<220> FEATURE:
<223> OTHER INFORMATION: Marinitoga piezophila

<400> SEQUENCE: 10

Tyr Ile Gly Ile Asp Leu Ser His Asp Glu Leu Asn Glu Lys Met Asn
1               5                   10                  15

Leu Asp Phe Ile Leu Arg Asp Gly Arg Phe Ile Leu His Ile Ala Asn
            20                  25                  30

Lys Val Ala Leu
        35

<210> SEQ ID NO 11
<211> LENGTH: 36
<212> TYPE: PRT
<213> ORGANISM: Artificial sequence
<220> FEATURE:
<223> OTHER INFORMATION: Natronobacterium gregoryi

<400> SEQUENCE: 11

Phe Ile Gly Ile Asp Val Ser Arg Ser Gln Leu Gly Glu Lys Leu Gln
1               5                   10                  15

Ser Thr Val Ile His Arg Asp Gly Phe Met Asn Thr Ala Tyr Ala Asp
            20                  25                  30

Gln Ala Ser Thr
        35

<210> SEQ ID NO 12
<211> LENGTH: 36
<212> TYPE: PRT
<213> ORGANISM: Artificial sequence
<220> FEATURE:
<223> OTHER INFORMATION: Limnothrix rosea

<400> SEQUENCE: 12

Ile Val Gly Leu Asp Val Ser Arg Arg Ile Asp Gly Glu Ile Leu Pro
1               5                   10                  15

Glu His Leu Ile His Arg Asp Gly Leu Phe Pro Thr Tyr Tyr Ala Asp
            20                  25                  30

Lys Ile Ser Thr
        35

<210> SEQ ID NO 13
<211> LENGTH: 36
<212> TYPE: PRT
<213> ORGANISM: Artificial sequence
<220> FEATURE:
<223> OTHER INFORMATION: Clostridium butyricum

<400> SEQUENCE: 13

```
Phe Ile Gly Leu Asp Val Gly Thr Arg Gln Ser Gly Glu Lys Ile Ala
1               5                   10                  15

Glu Thr Val Ile His Arg Asp Gly Phe Ser Arg Thr Gly Tyr Ala Asp
            20                  25                  30

Lys Ile Cys Lys
        35

<210> SEQ ID NO 14
<211> LENGTH: 36
<212> TYPE: PRT
<213> ORGANISM: Artificial sequence
<220> FEATURE:
<223> OTHER INFORMATION: Clostridium butyricum CWBI1009

<400> SEQUENCE: 14

Phe Ile Gly Leu Asp Val Gly Thr Arg Gln Ser Gly Glu Lys Ile Ala
1               5                   10                  15

Glu Thr Val Ile His Arg Asp Gly Phe Ser Arg Thr Gly

```
Thr Thr Ile His Arg Asp Gly Phe Trp Arg Ile His Tyr Ala Asp Leu
            20                  25                  30

Ser Ala Thr
        35

<210> SEQ ID NO 18
<211> LENGTH: 37
<212> TYPE: PRT
<213> ORGANISM: Artificial sequence
<220> FEATURE:
<223> OTHER INFORMATION: Mucilaginibacter paludis

<400> SEQUENCE: 18

Tyr Ile Gly Ile Asp Val His Asp Arg Ser Gln Arg Val Glu Lys Val
1               5                   10                  15

Arg Ala Lys Val Ile Val Arg Asp Gly Arg Ser Phe Ile Lys Leu Ile
            20                  25                  30

Asp Thr Leu Leu Glu
        35

<210> SEQ ID NO 19
<211> LENGTH: 37
<212> TYPE: PRT
<213> ORGANISM: Artificial sequence
<220> FEATURE:
<223> OTHER INFORMATION: Mucilaginibacter paludis double mutant

<400> SEQUENCE: 19

Tyr Ile Gly Ile Ala Val His Asp Arg Ser Gln Arg Val Glu Lys Val
1               5                   10                  15

Arg Ala Lys Val Ile Val Arg Ala Gly Arg Ser Phe Ile Lys Leu Ile
            20                  25                  30

Asp Thr Leu Leu Glu
        35

<210> SEQ ID NO 20
<211> LENGTH: 18
<212> TYPE: DNA
<213> ORGANISM: Artificial sequence
<220> FEATURE:
<223> OTHER INFORMATION: gDNA

<400> SEQUENCE: 20
tgaggtagta ggttgtat                                                18

<210> SEQ ID NO 21
<211> LENGTH: 18
<212> TYPE: RNA
<213> ORGANISM: Artificial sequence
<220> FEATURE:
<223> OTHER INFORMATION: gRNA

<400> SEQUENCE: 21
ugagguagua gguuguau                                                18

<210> SEQ ID NO 22
<211> LENGTH: 45
<212> TYPE: DNA
<213> ORGANISM: Artificial sequence
<220> FEATURE:
<223> OTHER INFORMATION: tDNA

<400> SEQUENCE: 22
```

```
aaacgacggc cagtgccaag cttactatac aacctactac ctcat            45

<210> SEQ ID NO 23
<211> LENGTH: 45
<212> TYPE: RNA
<213> ORGANISM: Artificial sequence
<220> FEATURE:
<223> OTHER INFORMATION: tRNA

<400> SEQUENCE: 23
aaacgacggc cagugccaag cuuacuauac aaccuacuac cucau            45
```

MBP_ARGONAUTE PROTEINS FROM PROKARYOTES AND APPLICATIONS THEREOF

TECHNICAL FIELD

The disclosure relates to the technical field of molecular biology, and more particularly to Mbp_Argonaute proteins from prokaryotes and applications thereof.

SEQUENCE LISTING

This application incorporates by reference the material in the sequence listing submitted via ASII text file titled 22009JHG-USP1-SL.txt, with the date of creation being Jun. 1, 2023, and the size of the ASCII text file being 17235 bytes. No new matter is entered.

BACKGROUND

Currently, eukaryotic Argonaute proteins (shorted as eAgos, also referred to as Argonaute proteins from eukaryotes) are capable of catalyzing Ribonucleic Acid (shorted as RNA) cleavage reactions guided by guide RNAs (shorted as gRNAs) under room temperature conditions, and play a key role in the RNA interference (shorted as RNAi) pathway in vivo. Prokaryotic Argonaute proteins (shorted as pAgos, also referred to as Argonaute proteins from prokaryotes) are more diverse in function and structure than the eAgos, but their physiological functions have long been elusive. Early studies focused on pAgos of thermophilic organisms, except for Argonaute proteins from *Marinitoga piezophila* (shorted as MpAgo) which favor the use of 5'-terminal hydroxylated (5'OH) guide DNA (shorted as gDNA) to cleave target single-stranded deoxyribonucleic acids (shorted as ssDNAs) and target RNAs, the other pAgos from thermophilic organisms favor the use of 5'-terminal phosphorylated (5'P) gDNA to cleave target ssDNAs and target RNAs. The pAgos from thermophilic organisms have low levels of cleavage activities of gDNA guided target ssDNAs and/or target RNAs under mesophilic conditions, which limits the application and development of pAgos-based RNA editing technologies. Recent studies have begun to focus on pAgos from mesophilic organisms, aiming at the finding of pAgos that can efficiently cleave target DNAs and/or target RNAs under mesophilic conditions.

Almost all of the characterized mesophilic pAgos prefer to catalyze gDNA-guided target DNA cleavage at mesophilic temperatures while having low RNA cleavage activities. An Argonaute protein from *Natronobacterium gregory* (shorted as NgAgo) can cleave a target RNA guided by gDNA at room temperature, but its cleavage site is uncertain, and it has not been shown to cleave highly-structured RNA. In addition, although eAgos are thought to have evolved from pAgos, currently characterized pAgos do not catalyze gRNA-guided target RNA cleavage reactions at mesophilic temperatures like the eAgos.

There has long been widespread interest in programmable endonucleases of target RNAs, as such endonucleases can be applied to RNA structure-function studies, nucleic acid detection fields, RNA nanotechnology, and RNA therapeutics. The early methods used have certain limitations, such as the need for extensive redesign or additional selective evolution for each target. The newly developed clustered regularly interspaced short palindromic repeat (CRISPR)/CRISPR-associated (Cas) nucleases are rapidly being applied in the fields of nucleic acid detection and viral clearance. However, CRISPR/Cas nucleases require the gRNA which must be transcribed and purified in vitro or purchased in a large quantity. In addition, CRISPR/Cas nucleases have not yet shown the ability to recognize structured RNA elements. Some eAgos are capable of cleaving almost all types of RNAs at mesophilic temperatures under the guide of gDNA, but RNAi pathways exist in most plant and animal cells, so that these eAgos may interfere with the cell's own RNAi function, which hinders the application of eAgos to intracellular RNA editing. There is no RNAi pathway in prokaryotic organisms, so pAgos may not affect the RNAi function of the cells themselves. There is still an urgent need in the field of RNA editing for pAgos that can function under room temperature and be applied to RNA editing in plant and animal cells.

The problems and defects of the prior art are that: RNA editing refers to a process of altering genetic information at a level of the messenger RNA (mRNA). RNA editing is related to biological cell development and differentiation, and is an important way of gene expression regulation. The prior art does not have pAgos that can effectively target cleave various types of RNAs under room temperature and be applied to RNA editing in plant and animal cells. General RNAi technology requires the use of double-stranded RNA (shorted as dsRNA), chemical synthesis of the dsRNA is expensive and has a long customization cycle, in vitro transcription of the dsRNA is relatively inexpensive but difficult and time-consuming to operate, and a gene interference effect of short hairpin RNA (shRNA) expression plasmid is durable and economical but time-consuming to prepare and there is non-specific gene suppression, etc. The CRISPR-based technology also requires the use of long gRNA, which has the same problems as RNAi technology, and in addition, Cas proteins (e.g. Cas13a) relies on a specific motif near the target site to recognize and bind the target, which limits the scope of what can be edited, Cas proteins have also been found to have very strong non-specific "collateral" activity, which raises concerns about their possible off-target responses.

SUMMARY

Purposes of the disclosure are to provide Mbp_Argonaute proteins from prokaryotes and applications thereof, the disclosure synthesizes an Argonaute protein gene derived from the psychrotolerant prokaryote *Mucilaginibacter paludis*, and names the protein as MbpAgo, it was found that the MbpAgo has binding activity for single-stranded guide DNA and nuclease activity for the target RNA and/or the target DNA complementarily paired with the single-stranded guide DNA. Thus, the MbpAgo can be used for target RNA editing in vivo and in vitro to achieve site-specific modification of genetic material. The MbpAgo not only allows modification of highly-structured RNAs, but also does not affect an endogenous RNAi pathway in plant and animal cells, and thus provides a new and powerful tool for RNA editing with high cleavage activity and good specificity.

The first purpose of the disclosure is to provide a Mbp_Argonaute protein, the Mbp_Argonaute protein consists of an amino acid sequence as shown in SEQ ID NO:1, or a sequence with at least 50% or at least 80% homology to the amino acid sequence as shown in SEQ ID NO:1.

In an embodiment, the Mbp_Argonaute protein consists of the sequence with at least 90%, more preferably at least 95% homology to the amino acid sequence as shown in SEQ ID NO:1.

In an embodiment, the Mbp_Argonaute protein consists of the sequence with at least 50% or at least 80% homology to non-catalytically active sites of the amino acid sequence as shown in SEQ ID NO:1.

In an embodiment, the Mbp_Argonaute protein consists of the sequence with at least 90%, more preferably at least 95% homology to the non-catalytically active sites of the amino acid sequence as shown in SEQ ID NO:1.

In an embodiment, the non-catalytically active sites of the amino acid sequence shown in SEQ ID NO:1 include sites other than sites at $562^{th}$-$570^{th}$ positions, at $597^{th}$-$606^{th}$ positions, at $631^{th}$-$639^{th}$ positions, and at $764^{th}$-$772^{th}$ positions of the amino acid sequence as shown in SEQ ID NO: 1.

In an embodiment, a length of the Mbp_Argonaute protein is 795 numbers of amino acids, or may be a longer or shorter stretch of contiguous amino acids, and the number of the amino acids (longer or shorter) may be any number from 1 to 1000.

The second purpose of the disclosure is to provide a gene encoding the above Mbp_Argonaute protein; the gene consists of a nucleotide sequence as shown in SEQ ID NO: 2, or a sequence with at least 50% or at least 80% homology with the nucleotide sequence as shown in SEQ ID NO: 2.

In an embodiment, the gene consists of the sequence with at least 90%, and more preferably, at least 95% homology with the nucleotide sequence as shown in SEQ ID NO: 2.

The third purpose of the disclosure is to provide a vector including the above gene.

The fourth purpose of the disclosure is to provide a cell including the above vector.

The fifth purpose of the disclosure is to provide a pAgo complex including: the above Mbp_Argonaute protein and a single-stranded guide DNA.

In an embodiment, a length of the single-stranded guide DNA is 8 to 40 numbers of nucleotides.

In an embodiment, the length of the single-stranded guide DNA is 12 to 30 numbers of nucleotides, and more preferably, 15 to 20 numbers of nucleotides, such as 16, 18 or 20 numbers of nucleotides.

In an embodiment, the single-stranded guide DNA is one of a 5'-terminal phosphorylated DNA and a 5'-terminal hydroxylated DNA.

The sixth purpose of the disclosure is to provide a use of the above Mbp_Argonaute protein, or the above vector, or the above cell, or the above pAgo complex for specifically cleaving a target RNA or a target DNA.

In an embodiment, the target RNA is not highly-structured, or is highly-structured; or the target RNA is a dsRNA; or the target RNA is an in vitro transcribed RNA; or the target RNA is a viral genomic RNA; or the target RNA is a mRNA; or the target RNA is one of other intracellular RNAs.

In an embodiment, the target DNA is one of a ssDNA and a double-stranded DNA (dsDNA).

The seventh purpose of the disclosure is to provide a method for specifically cleaving a target RNA or a target DNA, including: forming a pAgo complex by combining the above Mbp_Argonaute protein with a single-stranded guide DNA; and performing specific cleavage on the target RNA or the target DNA complementarily paired with the single-stranded guide DNA.

In an embodiment, the complementarily paired with the single-stranded guide DNA means that the single-stranded guide DNA is either completely complementary to the sequence of the same length contained in the target sequence, or there are many mismatches (usually separated or continuous), and the number of the mismatches may be 1, 2, 3, 4 or 5.

In an embodiment, the specific cleavage performed on the target RNA or the target DNA is at a temperature in a range of 4 Celsius degrees (° C.) to 65° C.

In an embodiment, the temperature is in a range of 30° C. to 55° C., and more preferably, 37° C.

In an embodiment, the pAgo complex specifically cleaves the target RNA or the target DNA in a buffer containing at least one divalent metal cation selected from a group consisting of manganese ion ($Mn^{2+}$), magnesium ion ($Mg^{2+}$), cobalt ion ($Co^{2+}$), and nickel ion ($Ni^{2+}$).

In an embodiment, a concentration of the at least one divalent metal cation is in a range of 0.05 millimoles per liter (mM) to 10 mM.

In an embodiment, a concentration of $Mn^{2+}$ is at least 0.05 mM or a concentration of $Mg^{2+}$ is at least 0.1 mM when the guide DNA is a 5'-terminal phosphorylated DNA.

The eighth purpose of the disclosure is to provide a kit including the above Mbp_Argonaute protein and a single-stranded guide DNA.

Compared with the prior art, the disclosure has the following beneficial effects.

(1) The disclosure provides an Argonaute protein derived from a psychrotolerant prokaryote *Mucilaginibacter paludis* and named the protein as MbpAgo, which has binding activity for the single-stranded guide DNA and nuclease activity for the target RNA and/or the DNA complementarily paired with the single-stranded guide DNA, thus the MbpAgo can be used for target RNA editing in vivo and in vitro to achieve site-specific modification of genetic material, which is a novel and effective tool to greatly promote the development of the RNA editing field.

(2) The MbpAgo can cleave highly secondary structured RNAs, and making it possible to cleave all types of RNAs.

(3) The MbpAgo does not depend on the special gene sequences near the target sites to recognize and bind the target sequence, thus the DNA guide is easy to design without considering the site restriction; and compared with the traditional guide RNA, the synthesis cycle of the guide DNA is short and inexpensive, which is greatly cost-saving.

(4) The MbpAgo has a strong cleavage activity that is strictly dependent on the complementary pairing of a guide and a target, without the non-specific "incidental cleavage" activity of CRISPR-related proteins, and with better specificity.

(5) The nuclease active site of the MbpAgo can be mutated to obtain the pAgo with a complete loss of cleavage activity, which can be fused to other effector proteins, and further expanding its application.

(6) The MbpAgo interferes with the RNAi pathway in plant and animal cells, avoiding the effect on the endogenous RNAi pathway in the plant and animal cells, and the MbpAgo has a protein size ratio of about three-quarters of the eAgos and one-half of the CRISPR-related proteins, and thus making it easier to transfect into cells.

BRIEF DESCRIPTION OF DRAWINGS

FIG. 3 illustrates a schematic diagram of sequence comparison of MbpAgo and characterized Ago proteins according to an embodiment 1 of the disclosure.

FIG. 4 illustrates a schematic diagram of sequences for testing the target DNA, the target RNA, the guide ssDNA and the guide ssRNA according to an embodiment 2 of the disclosure.

FIG. 5 illustrates a schematic diagram of results of detecting MbpAgo cleaving the ssRNA, and detecting the cleavage activity of *Mucilaginibacter paludism* double mutant Argonaute protein (MbpAgo_DM) to the target RNA according to an embodiment 2 of the disclosure.

DETAILED DESCRIPTION OF EMBODIMENTS

The technical schemes of the disclosure will be described clearly and completely below in combination with the embodiments of the disclosure. Obviously, the described embodiments are only part of the embodiments of the disclosure, not all of them. Based on the embodiments of the disclosure, all other embodiments obtained by those skilled in the art without creative labor belong to the protection scope of the disclosure.

Embodiment 1 MbpAgo Expression and Purification

A nucleotide sequence as shown in SEQ ID NO: 2 was amplified from the psychrotolerant prokaryote *Mucilaginibacter paludis* and ligated to pET28a using conventional methods to obtain pET28a-MbpAgo plasmids, which were then transformed into *Escherichia coli* Rosetta (DE3), and single colonies were inoculated into Luria-Bertani (LB) liquid medium containing 50 milligrams per milliliter (mg/mL) kanamycin and incubated in a shaker at 37° C. and 220 revolutions per minute (rpm). When the optical density 600 ($OD_{600}$) of the organism reached 0.8, it was moved to a shaker at 18° C. and induced overnight by isopropyl-beta-d-thiogalactopyranoside (IPTG). The organisms were collected by centrifugation at 6000 rpm for 10 minutes (min) and washed with Buffer A (Tris(hydroxymethyl)methyl aminomethane THAM-hydrochloride (shorted as Tris-HCl) with 20 mM and *pondus hydrogenii* (pH) 7.4, Sodium chloride (shorted as NaCl) with 500 mM, and imidazole with 10 mM), the bacteria were resuspended in Buffer A, Phenylmethylsulfonyl fluoride (shorted as PMSF) with a final concentration of 1 mM was added, and the bacteria were crushed at high pressure. 18000 rpm centrifugation was performed for 30 min and the supernatant was collected. The supernatant was filtered and then purified by Nickel ion metal chelating affinity chromatography medium (Ni-NTA).

Ten column volumes of 20 mM imidazole each (added in three parts), and three column volumes of 50 mM, 80 mM, 100 mM, 150 mM, 200 mM, 250 mM, 300 mM, and 1 M each were washed, and samples were taken for SDS-PAGE detection. The eluted fractions containing high purity target proteins were collected and ultrafiltered to Buffer B (Tris-HCl with 20 mM and pH 7.4, NaCl with 500 mM, and Tris(2-carboxyethyl)phosphine (TCEP) with 1 mM). The proteins purified by Ni-NTA were purified by molecular sieves (Superdex™ 200 16/600 column, GE Healthcare), which were pre-equilibrated with Buffer B. The purified proteins were collected, identified for purity and analyzed by SDS-polyacrylamide gel, divided into small portions, snap-frozen in liquid nitrogen and stored at −80° C.

Figure 1:
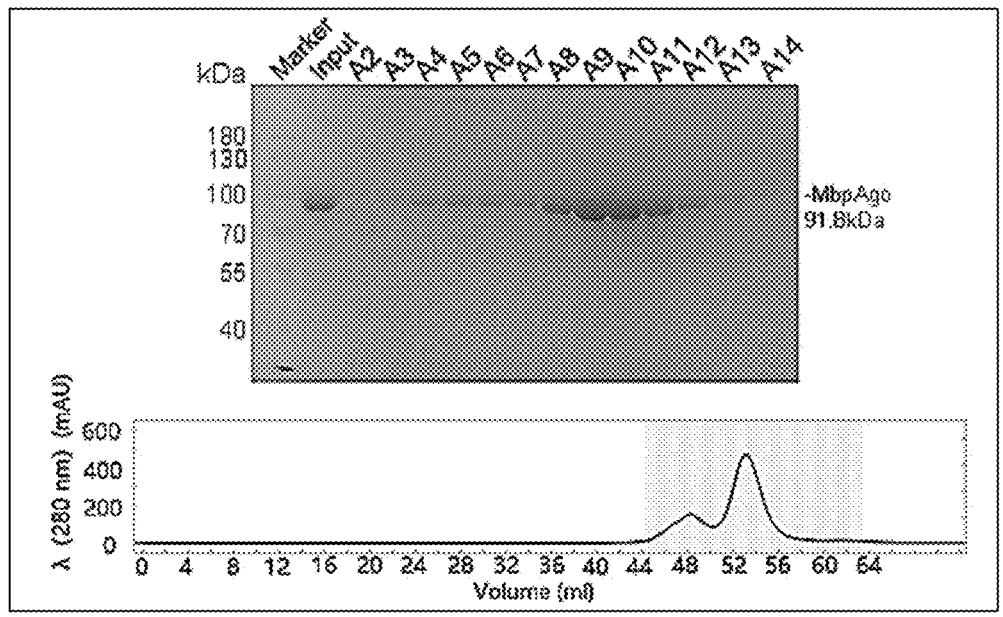
FIG. 1 illustrates a schematic diagram of MbpAgo purity analyzed by the sodium dodecyl sulfate-polyacrylamide gel electrophoresis (SDS-PAGE) gel according to an embodiment 1 of the disclosure.
Figure 2:
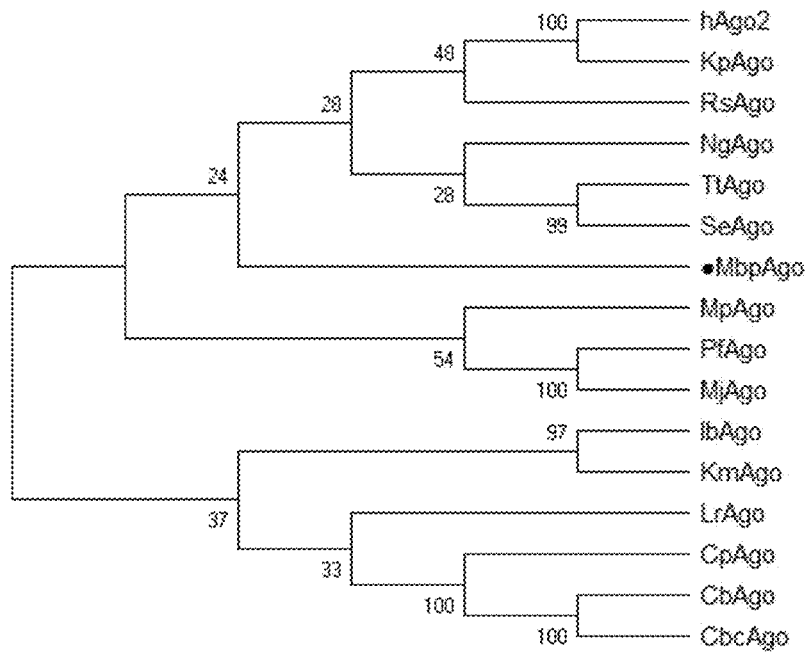
FIG. 2 illustrates a schematic diagram of an evolutionary tree of MbpAgo and some characterized Argonaute proteins according to an embodiment 1 of the disclosure.

The result of the SDS-polyacrylamide gel identification analysis is illustrated in FIG. 1, and an expected size of MbpAgo is 91.8 kilo Dalton (kDa) by using www.expasy.org/ to calculate, and its amino acid sequence is shown in SEQ ID NO: 1. The evolutionary tree of the MbpAgo and some of the characterized Argonaute proteins (Ago proteins) is illustrated in FIG. 2, and the sequence comparison of the catalytic DEDX quadruplex of MbpAgo and seventeen characterized Ago proteins is shown in FIG. 3.

Embodiment 2 MbpAgo Cleavage Activity Detection

In order to evaluate which combinations of guide RNA/DNA and target RNA/DNA MbpAgo can cleave, the activity of all possible combinations was detected. The schematic diagram of sequences of the target DNA, the target RNA, the guide ssDNA and the guide ssRNA is illustrated in FIG. 4, and the arrows represent the predicted cleavage sites.

Figure 6:
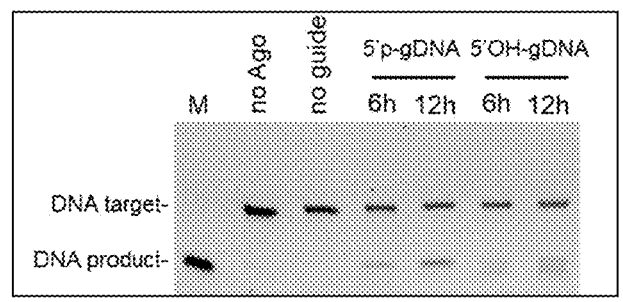
FIG. 6 illustrates a schematic diagram of a result of detecting MbpAgo cleaving the target ssDNA according to an embodiment 2 of the disclosure.

The cleavage experiments were all performed at 37° C. in a 4:2:1 (MbpAgo: guide: target) molar ratio. 800 nanomoles per liter (nM) MbpAgo was mixed with 400 nM guide in a reaction buffer containing 4-(2-hydroxyethyl)-1-piperazine ethanesulfonic acid (shorted as HEPES)-Sodium hydroxide (NaOH) with 10 mM and pH 7.5, NaCl with 100 mM, Manganese (II) chloride (shorted as $MnCl_2$) with 5 mM and 5% glycerol and incubated at 37° C. for 10 min for guide loading. The nucleic acid target was added to 200 nM. After 1 hour (h) of reaction at 37° C., the reaction was terminated by mixing the sample with 2×RNA loading dye (95% formamide, 18 mM Edetic acid (EDTA) and 0.025% SDS and 0.025% bromophenol blue) and heating at 95° C. for 5 min. The cleavage products were resolved by 20% denaturing PAGE, stained with SYBR Gold (Invitrogen) and visualized with Gel Doc™ XR+ (Bio-Rad). The result of the cleavage of the target ssRNA is illustrated in FIG. 5, and the result of the cleavage of the target ssDNA is illustrated in FIG. 6.

The results showed that no product band (34nt) was observed in the DNA/RNA (guide/target) control determination incubated without MbpAgo (no Ago lane), indicating that the formation of the product band was the result of MbpAgo nuclease activity. MbpAgo can cleave the target RNA and DNA with the 5'phosphorylated guide DNA and the 5' hydroxylated guide DNA, but cannot use the RNA as a guide. FIG. 5 illustrates that the MbpAgo can cleaves the target ssRNA after binding the ssDNA guide, and FIG. 6 illustrates that the MbpAgo can cleaves the target DNA after binding the ssDNA guide.

Embodiment 3 Effect of gDNA Length on Target RNA Cleavage Activity

Figure 7:
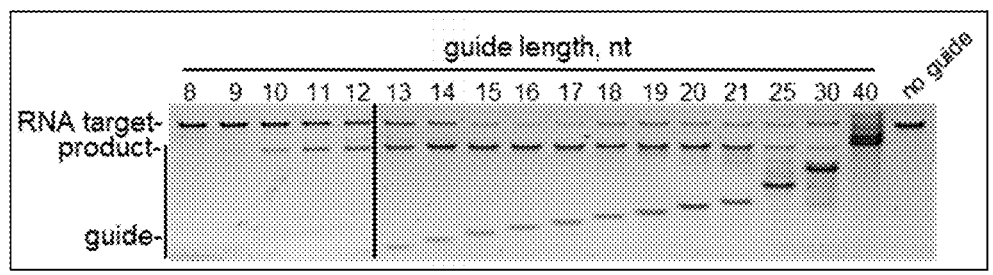
FIG. 7 illustrates a schematic diagram of a result of urea/polyacrylamide gel detection of a product of MbpAgo cleaving the target RNA with the guide DNA of different lengths according to an embodiment 3 of the disclosure.

DNAs with length from 8 nt to 40 nt were selected as guide DNAs respectively, and incubated with the MbpAgo to form the pAgo complexes, and the activities of different lengths of guide DNAs on the recognition and cleavage of the target RNAs by the MbpAgo were measured. The results of the detection are illustrated in FIG. 7.

The results show that the length of the guide DNA has an effect on the activity of the MbpAgo in recognizing and cleaving the target RNA, where the target RNA can be effectively cleaved when the range of the guide DNA length is in a range of 8 to 40 nt, and preferably the length is in a range of 10 nt to 30 nt.

Figure 8:
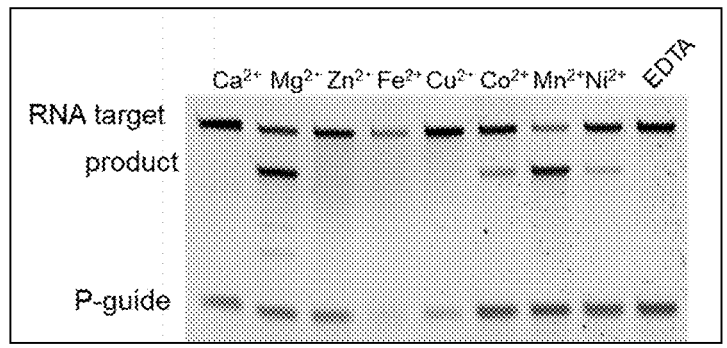
FIG. 8 illustrates a schematic diagram of a result of urea/polyacrylamide gel detection of a product of the MbpAgo cleaving the target RNA under different divalent metal cations according to an embodiment 4 of the disclosure.

Embodiment 4 Effect of Divalent Metal Ions and their Concentration on Target RNA Cleavage Activity The MbpAgo and the guide DNA were mixed in a reaction buffer containing HEPES-NaOH with 10 mM and pH 7.5, NaCl with 100 mM, divalent metal cations with 5 mM and 5% glycerol and incubated at 37° C. for 10 min for guide loading, followed by the addition of target sequences for cleavage activity detection. The divalent metal cations were selected from $Mn^{2+}$, $Mg^{2+}$, $Ca^{2+}$, $Cu^{2+}$, $Fe^{2+}$, $Co^{2+}$, $Zn^{2+}$ and $Ni^{2+}$, and the effects of different metal cations on the cleavage activity were measured, and the results are illustrated in FIG. 8. The results showed that the selection of divalent metal cations had an effect on the cleavage activity of the MbpAgo, and the target RNA can be effectively cleaved at $Mn^{2+}$, $Mg^{2+}$, $Co^{2+}$, and $Ni^{2+}$ conditions.

Figure 9:
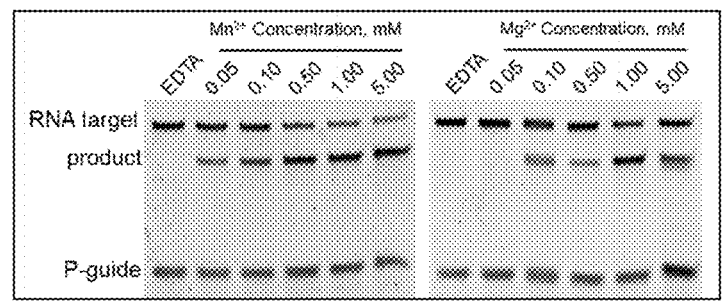
FIG. 9 illustrates a schematic diagram of a result of urea/polyacrylamide gel detection of a product of the MbpAgo cleaving the target RNA under different concentrations of $Mn^{2+}$ or $Mg^{2+}$ according to an embodiment 4 of the disclosure.

The minimum concentration of divalent metal ions was further mapped, and $Mn^{2+}$ or $Mg^{2+}$ from 0.05 mM to 5.00 mM were selected to be added to the buffer respectively, and the cleavage activity of the MbpAgo on the target RNA was measured after 15 min of reaction, and the result is illustrated in FIG. 9. The result showed that the concentration of divalent metal cations had an effect on the cleavage activity of MbpAgo. When the guide is 5' phosphorylated DNA, the target RNA can be efficiently cleaved at a minimum $Mn^{2+}$ concentration of 0.05 mM or a minimum $Mg^{2+}$ concentration of 0.1 mM. i.e., the added concentration of $Mn^{2+}$ should be greater than or equal to 0.05 mM, while the added concentration of $Mg^{2+}$ should be greater than or equal to 0.1 mM.

Figure 10:
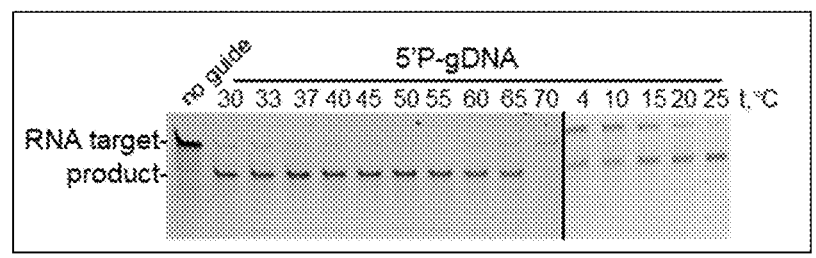
FIG. 10 illustrates a schematic diagram of a result of urea/polyacrylamide gel detection of a product of the MbpAgo cleaving the target RNA under different temperatures according to an embodiment 5 of the disclosure.

Embodiment 5 Effect of Temperature on the Cleavage Activity of MbpAgo on Target RNA After MbpAgo was incubated with the guide DNA to form a complex, the target sequence was added, and the cleavage activity was measured after reacting at 4~70° C. for 15 min respectively, and the results are illustrated in FIG. 10. The result showed that the target RNA could be cleaved when the guide was 5' phosphorylated DNA and the temperature was from 4 to 65° C., where the cleavage activity was relatively high from 30 to 55° C., i.e., the MbpAgo could cleave the target gene under a wider range of temperature conditions.

Embodiment 6 Cleavage Effect of MbpAgo on Highly-Structured Target RNA

Figure 11:
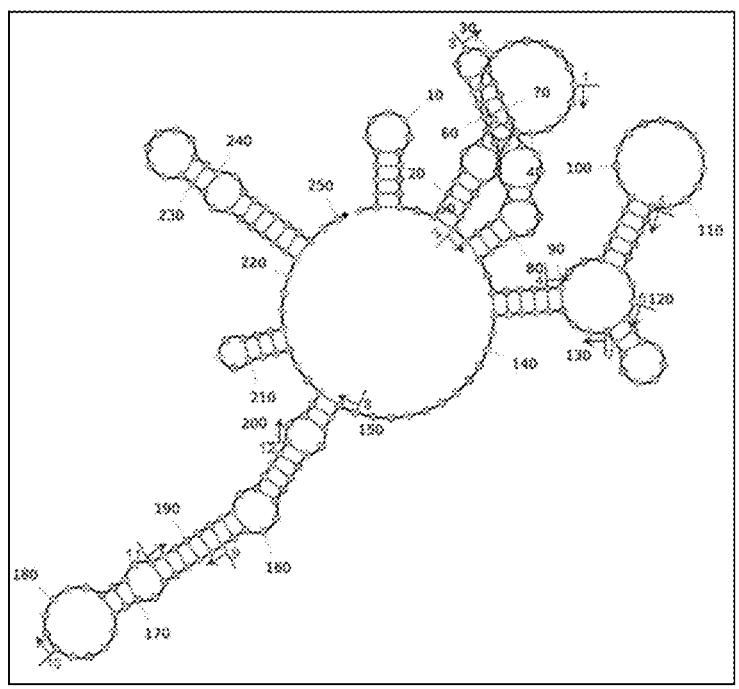
FIG. 11 illustrates a schematic diagram of a sequence structure of the local RNA of highly-structured severe acute respiratory syndrome coronavirus 2 (SARS-Cov2) RNA replicase (RdRp) and a design of a targeting region of the guide DNA according to an embodiment 6 of the disclosure.
Figure 12:
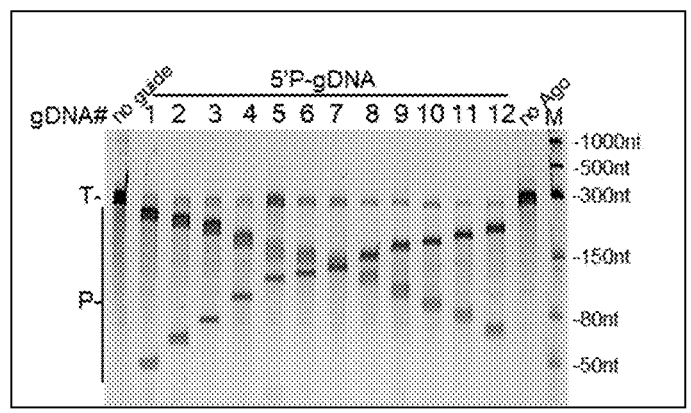
FIG. 12 illustrates a schematic diagram of a result of urea/polyacrylamide gel detection of a product of MbpAgo cleaving the highly-structured target RNA according to an embodiment 7 of the disclosure.

SARS-Cov2 RdRp is the presence of a highly-structured RNA with the predicted local structure illustrated in FIG. 11. The local RNA of SARS-Cov2 RdRp was transcribed in vitro using T7 RNA polymerase and a synthetic DNA template with a T7 promoter sequence. The transcripts used for the cleavage detection were treated with DNase I and gel purified. Twelve gDNAs (18 nt in length, targeting regions as illustrated in FIG. 11) were designed separately to guide MbpAgo for cleavage at different sites. The guide DNA was incubated with MbpAgo at room temperature for 10 min, and then reacted at 37° C. for 30 min, and the results were measured as illustrated in FIG. 12. The results showed that cleavage products were detected at the expected positions in all sites, albeit to different degrees, indicating that the MbpAgo-gDNA complex cleaves target RNA sequences even in highly-structured RNAs, i.e., MbpAgo can cleave highly-structured target RNAs under mesophilic conditions.

Embodiment 7 MbpAgo Catalytic Active Site Mutation

FIG. 2 has shown the MbpAgo catalytic quadruplex DEDD, which respectively are sites at $562^{th}$-$570^{th}$ positions, at $597^{th}$-$606^{th}$ positions, at $631^{th}$-$639^{th}$ positions and at $764^{th}$-$772^{th}$ positions of the sequence shown in SEQ ID NO: 1. By mutating one or more amino acid residues essential for the catalytic activity of the MbpAgo protein to form a new nuclease activity, particularly the deletion of nucleic acid endonuclease activity. For example, for the MbpAgo catalytic quadruplex, its amino acid sequence shown as SEQ ID NO:18, is that:

YIGIDVHDR

SQRVEKVRAK

VIVRDGRSF

IKLIDTLLE

The 1st and 3rd D were mutated to A to obtain the double mutant DM and its cleavage activity for the target RNA was determined, and the results of the detection are shown in the last two lanes (DM) of FIG. 5, which show that mutation of the MbpAgo catalytic quadruplex causes it to lose the activity of DNA-guided cleavage of the target RNA. That is, mutation of at least one amino acid located in the evolutionarily conserved amino acid tetrad can alter the catalytic activity of the MbpAgo protein. That is, the quadruplex is key sites for MbpAgo catalytic activity.

The disclosure further provides an in vitro method for site-specific targeted blocking of target DNA or target RNA, including the following steps: providing the pAgo without nuclease activity as described herein and the ssDNA guide, the guide and the pAgo forming a pAgo-guide complex;

contacting the pAgo-guide complex with the target RNA or the target DNA, the target RNA or the target DNA having a nucleotide sequence that is mostly complementary to the sequence of the guide, and the pAgo-guide complex binding to a region on the target that is mostly complementary to the guide.

The above described are only exemplary embodiments of the disclosure, but the scope of protection of the disclosure is not limited thereto, and any amendment or replacement readily conceivable by those skilled in the art within the scope of the technology disclosed herein shall be covered by the scope of protection of the disclosure.

What is claimed is:

1. A method of application of a prokaryotic Argonaute protein (pAgo) complex, comprising:

forming the pAgo complex by combining a Mbp_Argonaute protein with a single-stranded guide Deoxyribo-Nucleic Acid (DNA); and performing specific cleavage, with the pAgo complex, on a target RNA or a target DNA complementarily paired with the single-stranded guide DNA in a buffer containing 4-(2-hydroxyethyl)-1-piperazine ethanesulfonic acid-sodium hydroxide (HEPES-NaOH), sodium chloride (NaCl) and a divalent metal cation, wherein the divalent metal cation is selected from the group consisting of manganese ion ($Mn^{2+}$), magnesium ion ($Mg^{2+}$), cobalt ion ($Co^{2+}$), and nickel ion ($Ni^{2+}$);

wherein the Mbp_Argonaute protein consists of the amino acid sequence of SEQ ID NO:1.

2. The method according to claim 1, wherein the Mbp_Argonaute protein is encoded by a gene; and the gene consists of the nucleotide sequence of SEQ ID NO: 2.

3. The method according to claim 1, wherein a length of the single-stranded guide DNA is 8 to 40 numbers of nucleotides.

4. The method according to claim 1, wherein the single-stranded guide DNA is one of a 5'-terminal phosphorylated DNA and a 5'-terminal hydroxylated DNA.

5. The method according to claim 1, wherein the target RNA is not highly-structured RNA; or is highly-structured RNA; double-stranded RNA (dsRNA); in vitro transcribed RNA; viral genomic RNA; messenger RNA (mRNA); or intracellular RNA.

6. The method according to claim 1, wherein the target DNA is one of a single-stranded DNA (ssDNA) and a dsDNA.

7. The method according to claim 1, wherein the specific cleaving performed on the target RNA or the target DNA is at a temperature in a range of 4 Celsius degrees (° C.) to 65° C.

8. The method according to claim 1, wherein a concentration of the divalent metal cation is in a range of 0.05 millimoles per liter (mM) to 10 mM.

9. The method according to claim 1, wherein the single-stranded guide DNA is 5' phosphorylated DNA, when the divalent metal cation is $Mn^{2+}$, a concentration of $Mn^{2+}$ is greater than or equal to 0.05 mM, and when the divalent metal cation is $Mg^{2+}$, a concentration of $Mg^{2+}$ is greater than or equal to 0.1 mM.

* * * * *